United States Patent
Ahn et al.

(10) Patent No.: US 8,143,470 B2
(45) Date of Patent: Mar. 27, 2012

(54) METHOD OF PURIFYING OLEFINS USING PYRROLIDINIUM-BASED OR PIPERIDINIUM-BASED IONIC LIQUIDS COMPRISING COPPER (I) HALIDE

(75) Inventors: Byoung Sung Ahn, Seoul (KR); Gyeong Taek Gong, Seoul (KR); Hoon Sik Kim, Seoul (KR); Minserk Cheong, Seoul (KR); Jin Hyung Kim, Seoul (KR)

(73) Assignee: Kolon Industries, Inc., Incheon (KR)

( * ) Notice: Subject to any disclaimer, the term of this patent is extended or adjusted under 35 U.S.C. 154(b) by 264 days.

(21) Appl. No.: 12/698,615

(22) Filed: Feb. 2, 2010

(65) Prior Publication Data

US 2011/0092758 A1    Apr. 21, 2011

(30) Foreign Application Priority Data

Oct. 20, 2009    (KR) .................. 10-2009-0099482

(51) Int. Cl.
*C07C 7/156* (2006.01)

(52) U.S. Cl. ........ 585/847; 585/843; 585/844; 585/845; 585/809; 585/849

(58) Field of Classification Search .................. None
See application file for complete search history.

(56) References Cited

U.S. PATENT DOCUMENTS

| | | |
|---|---|---|
| 3,755,448 A | 8/1973 | Merianos et al. |
| 3,758,603 A | 9/1973 | Steigelmann et al. |
| 3,792,981 A | 2/1974 | Hettick et al. |
| 4,019,879 A | 4/1977 | Rabo et al. |
| 4,034,065 A | 7/1977 | Kasai et al. |
| 4,318,714 A | 3/1982 | Kimura et al. |
| 4,717,398 A | 1/1988 | Pearce |
| 6,339,182 B1 * | 1/2002 | Munson et al. ............... 585/809 |
| 6,623,659 B2 * | 9/2003 | Munson et al. ............... 252/184 |

FOREIGN PATENT DOCUMENTS

| | | |
|---|---|---|
| DE | 2 059 794 | 6/1971 |
| JP | 61-050929 | 3/1986 |

OTHER PUBLICATIONS

Safarik, Douglas J. and Eldridge, R. Bruce, "Olefin/Paraffin Separations by Reactive Absorption: a Review," *Ind. Eng. Chem. Res.*, 1998, 37:2571-2581.

* cited by examiner

*Primary Examiner* — Tam M Nguyen
(74) *Attorney, Agent, or Firm* — Ladas & Parry LLP

(57) ABSTRACT

The present invention relates to a method of purifying olefin, the method comprising removing a small amount of acetylenic compounds contained in olefin by using pyrrolidinium-based or piperidinium-based ionic liquid mixtures comprising copper (I) halide. According to the method of the present invention, copper (I) halide is stabilized by pyrrolidinium-based or piperidinium-based ionic liquids, suppressing the oxidation of Cu(I) into Cu(II), whereby the capacity of removing acetylenic compounds can be maintained for a long time and the selective removal rate of acetylenic compounds to olefin can be significantly improved. In addition, since the ionic liquid mixtures comprising copper (I) halide used in the method of the present invention can be applied to both absorption and extraction processes, it can effectively remove acetylenic compounds from olefin in a more simple and economical way compared to the existing adsorption and membrane separation processes.

12 Claims, No Drawings

METHOD OF PURIFYING OLEFINS USING PYRROLIDINIUM-BASED OR PIPERIDINIUM-BASED IONIC LIQUIDS COMPRISING COPPER (I) HALIDE

The present application claims priority to Korean Patent Application No. 10-2009-99482, filed on Oct. 20, 2009, the subject matter of which is incorporated herein by reference in its entirety.

FIELD OF THE INVENTION

The present invention relates to a method of purifying olefins by removing small amounts of acetylenic compounds contained in olefins using pyrrolidinium-based or piperidinium-based ionic liquid mixtures comprising copper (I) halide.

BACKGROUND OF THE INVENTION

Olefins are mainly obtained by cracking naphtha or natural gas, but their purification requires a rather complicated and costly process because of the co-production of small amounts of acetylenic hydrocarbons with similar boiling points. Acetylenic compounds present in olefins can serve as catalyst poisons in the olefin polymerization process and also lower the product quality of the resulting polyolefins. Furthermore, the acetylenic compounds are sometimes converted into solids, blocking the fluid stream and even leading to explosion. Therefore, it is crucial to eliminate even the small amount of acetylenic compound contained in olefin.

The removal of acetylenes present in olefins may be commercially accomplished through a partial hydrogenation of acetylenes into olefins using a noble metal catalyst like supported Pd. However, olefins produced from the hydrogenation of acetylenes, as well as feed olefins, may undergo an over-hydrogenation reaction to produce paraffins, thus resulting in the loss of olefins. Furthermore, there may be severe catalyst poisoning resulting from the carbon deposition, and additional steps for regenerating the catalysts are required, as described in U.S. Pat. Nos. 3,755,448 and 3,792,981.

Solvent extraction using organic solvents, such as DMF (N,N-dimethylformamide) or NMP (N-methylpyrrolidinone), is another commercial process for separating acetylenes from the cracking process. Acetylenes thus obtained as the unavoidable by-products from the cracking process are the major source of acetylenes used for various organic syntheses. However, the extraction process is also technically disadvantageous and uneconomical, particularly due to the significant loss of solvent after multiple operations and to the low selectivity of acetylenes over olefins.

In some cases, the separation of unsaturated compounds from saturated hydrocarbon mixtures may also be carried out by energy intensive low temperature distillations.

With respect to solid adsorption, U.S. Pat. Nos. 4,019,879 and 4,034,065 teach methods for adsorbing and removing unsaturated compounds such as CO by using molecular sieves; however, these methods are not only limiting in terms of the adsorption capacity but also require a high temperature and high vacuum pressure for the stripping step.

To circumvent the problems encountered in conventional hydrogenation, solvent extraction, and low temperature distillation, separation through reversible π-complexation using a Ag(I) or Cu(I) salt has been discussed extensively.

Thus, U.S. Pat. No. 4,717,398 provides a method for removing unsaturated compounds by pressure swing with an adsorbent comprising faujasite zeolite substituted with Cu(I).

In addition, Japanese Patent Laid-Open Publication No. 1986-50929 discloses a method for removing acetylenic compounds by using an adsorbent comprising alumina, silica or active carbon loaded with Cu(I) or Ag(I) compounds; however, this method is problematic because the acetylenic compounds are likely to react with Cu(I) or Ag(I) to produce unstable copper- or silver-acetylides. Therefore, there is a demand for the development of an improved adsorbent that can prevent production of these materials.

German Patent No. 2059794 teaches a method of removing unsaturated compounds comprising acetylenic compounds by using a liquid absorbent mainly consisting of Cu(I) compounds and alkanolamines such as monoethanolamines; however, this method has the drawback of requiring an additional purification device due to the contamination of the final product by alkanolamines and co-absorption of olefin. Safarik D J, et al., *Ind. Eng. Chem. Res.* Vol 37, No. 7, 2571-2581, 1998 discloses a method of separating unsaturated compounds from paraffin by using a Cu(I) or Ag(I) compound solution which is subject to a reversible reaction with olefin and acetylene; however, this method is also problematic in that it requires a complicated regeneration process because of the low stability of the adsorbent.

As for membrane separation, U.S. Pat. No. 3,758,603 discloses a method of separating unsaturated compounds from saturated compounds by using liquid membranes prepared by loading silver salts with microporous membranes. According to the above method, however, salts for facilitated transport are likely to be washed away and solvents are easily volatilized, thereby making it difficult to maintain separation efficiency for a long time. U.S. Pat. No. 4,318,714 describes a method of using ion exchange resin membranes in which cations are substituted with anions, in order to prevent the silver ions from being washed away. In such cases where fixed liquid membranes are used, since facilitated transport only takes place when moisture exists, it is a nuisance to have to maintain the moisture level inside the membranes constant and remove the moisture again after the separation. In addition, not only is the above method impractical since it requires a membrane thickness of from 100 to 500 μm but the separation efficiency is also low.

Therefore, in addition to the formation of explosive acetylides, the unsatisfactory selectivity of acetylenes over olefins due to the similar bonding strength of acetylenes and olefins to Ag(I) or Cu(I) salt has always been problematic. Hence, there has been high interest in the field to search for efficient sorbents that can selectively and reversibly interact with acetylenes.

SUMMARY OF THE INVENTION

It is an objective of the present invention to solve the problems in the prior art, as discussed above. It is another objective of the present invention to provide a method of purifying olefin that is more simple and economical compared to the existing adsorption and membrane separation processes and is capable of removing acetylenic compounds from olefin at a high selective removal rate.

In order to achieve the above objectives, the present invention provides a method of purifying olefin, the method comprising removing acetylenic compounds from olefin by using pyrrolidinium-based or piperidinium based-ionic liquid mixtures comprising copper (I) halide.

In addition, the present invention provides pyrrolidinium-based or piperidinium-based ionic liquid mixtures comprising copper (I) halide for removing acetylenic compounds from olefin.

According to the method of purifying olefin in accordance with the present invention, copper (I) halide is stabilized by ionic liquids, suppressing the oxidation of Cu(I) into Cu(II), whereby the capacity of removing acetylenic compounds can be maintained for a long time and the selective removal rate of acetylenic compounds to olefin can be significantly improved. In addition, since the pyrrolidinium-based or piperidinium-based ionic liquid mixtures comprising copper (I) halide used in the method of the present invention can be applied to both absorption and extraction processes, they can remove acetylenic compounds from olefin in a more simple and economical way compared to the existing adsorption and membrane separation processes.

DETAILED DESCRIPTION OF THE INVENTION

In order to effectively remove acetylenic compounds from olefin, the present invention uses pyrrolidinium-based or piperinidium-based ionic liquid mixtures comprising copper (I) halide.

Specifically, the method of purifying olefin according to the present invention comprises the following steps:

1) preparing an ionic liquid mixture comprising copper (I) halide by dissolving copper (I) halide represented by Formula 1 in a pyrrolidinium-based ionic liquid represented by Formula 2 or a piperidinium-based ionic liquid represented by Formula 3; and 2) mixing said ionic liquid mixture comprising copper (I) halide with olefin and then reacting the resulting mixture by stirring to remove acetylenic compounds from olefin:

CuX  [Formula 1]

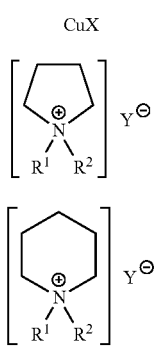

[Formula 2]

[Formula 3]

wherein X is Cl, Br or I,
$R^1$ is an $C_1\sim C_6$ alkyl group,
$R^2$ is an $C_1\sim C_6$ alkyl group or alkoxy group,
Y is a phosphite anion represented by Formula 4 or a phosphate anion represented by Formula 5,

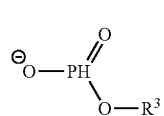

[Formula 4]

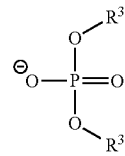

[Formula 5]

wherein $R^3$ is a $C_1\sim C_6$ alkyl group.

When copper (I) halide of Formula 1 is dissolved in a pyrrolidinium-based ionic liquid of Formula 2 or in a piperidinium-based ionic liquid of Formula 3 according to the present invention, the copper (I) halide is reacted with a phosphite anion of the pyrrolidinium-based ionic liquid or a phosphate anion of the piperidinium-based ionic liquid and then converted into an ionic liquid mixture represented by Formulae 6 and 7.

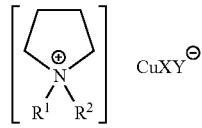

[Formula 6]

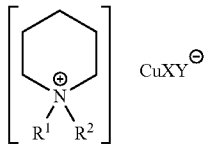

[Formula 7]

wherein X, $R^1$, $R^2$ and Y are as defined above.

The above conversion process can be illustrated by the following Reaction Schemes 1 and 2, in which the pyrrolidinium-based ionic liquid of Formula 2 and the piperidinium-based ionic liquid of Formula 3 must be capable of completely dissolving copper (I) halide of Formula 1 and can be used alone or in the form of a mixture of two or more.

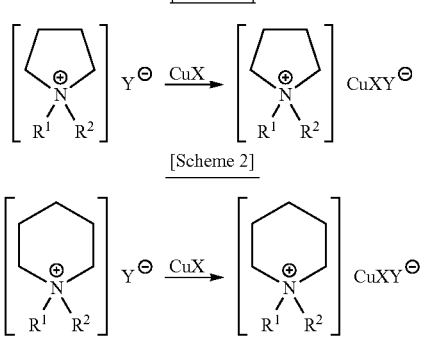

wherein, X, $R^1$, $R^2$ and Y are as defined above.

Copper (I) halides are generally not soluble in organic solvents and are likely to be oxidized by reacting with an alcohol or an amine and the like and produce an explosive acetylide by reacting with acetylenes. However, unlike the copper (I) halides, ionic liquid mixtures having the structures of Formulae 6 and 7 are not easily oxidized. Further, since the interaction between the above ionic liquid mixtures and the hydrogen atom of acetylenic compounds is rather weak, they do not produce an acetylide. Moreover, copper (I) halides, upon interaction, bind to double-bond compounds and triple-bond compounds with a similar strength, and thus cannot selectively remove only triple-bond compounds, whereas $CuXY^-$ in the ionic liquid mixtures of Formulae 6 and 7, although the binding strength to double-bond compounds and triple-bond compounds is slightly low, binds more strongly to triple-bond compounds than to double-bond compounds, and thus, is more effective in removing a very small amount of acetylenic compounds contained in olefin.

In step 1), the amount of copper (I) halide of Formula 1 dissolved in the pyrrolidinium-based ionic liquid of Formula 2 or in the piperidinium-based ionic liquid of Formula 3 may be from 5 to 50 parts by weight, specifically from 10 to 30 parts by weight, per 100 parts by weight of the pyrrolidinium-based or piperidinium-based ionic liquid. If the dissolved amount of copper (I) halide is less than 5 parts by weight, the capacity of the obtained ionic liquid mixture for removing acetylenic compounds decreases; and if the dissolved amount is greater than 50 parts by weight, the viscosity of the obtained ionic liquid mixtures increases, thereby leading to difficulties with the process.

In step 2), when mixing the ionic liquid mixture comprising copper (I) halide prepared in step 1) with olefin, the amount of olefin mixed may be from 20 to 500 parts by weight, specifically, from 50 to 200 parts by weight, per 100 parts by weight of the above ionic liquid mixture. If the amount of olefin is less than 20 parts by weight, productivity deteriorates; and if the amount is greater than 500 parts by weight, the removal rate of triple-bond compounds decreases, thereby requiring a multi-phase absorption or extraction process and causing an inconvenience.

In step 2), in order to remove a small amount of acetylenic compounds contained in the ionic liquid mixture comprising copper (I) halide according to the present invention, both the absorption and extraction processes may be applied. From the aspect of energy consumption, the absorption process is desirable for olefin in the gaseous state, while the extraction process is desirable for olefin in the liquid state. In other words, if olefin has 2 to 4 carbon atoms ($C_2$~$C_4$), it is present in a gaseous state at room temperature, and thus, acetylenic compounds may be removed by absorption; meanwhile, if olefin has at least 5 carbon atoms ($C_5$), it is present in a liquid state at room temperature, and thus, a liquid extraction process or an absorption process comprising vaporization may be used. In one embodiment of the present invention, a liquid olefin sample may be mixed with the ionic liquid mixture comprising copper (I) halide according to the present invention. If the mixture is subject to extraction, separation of layers takes place where the lower layer comprises the ionic liquid containing acetylenic compounds extracted from olefin and the upper layer comprises olefin, thereby making it easy to obtain purified olefin.

When removing acetylenic compounds from olefin by absorption or extraction, it is desirable to mix the ionic liquid mixture comprising copper (I) halide with olefin and extract the resulting mixture by stirring at 0 to 100° C. from 0.5 to 1 hr. The extraction temperature may be from 0 to 100° C., specifically from 20 to 50° C. If the extraction temperature is lower than 20° C. or higher than 50° C., it may result in unnecessary energy consumption, which is uneconomical.

Acetylenic compounds that can be removed from olefin according to the method of the present invention may be selected from the group consisting of acetylene, methylacetylene, 1-butyne, isopropenylacetylene and a mixture thereof.

The method of the present invention may further comprise a step comprising subjecting the ionic liquid mixture comprising copper (I) halide to layer separation after contacting the ionic liquid mixture comprising copper (I) halide with olefin, and regenerating the ionic liquid mixture by stripping under the conditions of 20-120° C. and 1-200 mmHg. The regeneration temperature during stripping may be from 20 to 120° C., specifically from 50 to 100° C. If the regeneration temperature is lower than 50° C., the regeneration efficiency declines, but if it is higher than 100° C., portions of the ionic liquid mixture comprising copper (I) halide can possibly be decomposed. In addition, the vacuum pressure during stripping may be from 1 to 200 mmHg, but specifically from 50 to 100 mmHg from an industrial viewpoint. If the vacuum pressure is higher than 100 mmHg, stripping capacity decreases, while if it is lower than 50 mmHg, energy consumption increases.

As discussed above, according to the method of the present invention, copper (I) halide is stabilized by ionic liquids, suppressing the oxidation of Cu(I) into Cu(II), whereby the capacity of removing acetylenic compounds can be maintained for a long time and the selective removal rate of acetylenic compounds to olefin can be significantly improved. In addition, since the pyrrolidinium-based or piperidinium-based ionic liquid mixtures comprising copper (I) halide used in the methods of the present invention can be applied to both absorption or extraction processes, they can remove acetylenic compounds from olefin in a more simple and economical way compared to the existing adsorption and membrane separation processes. In particular, the pyrrolidinium-based or piperidinium-based ionic liquid mixtures comprising copper (I) halide of the present invention have the following advantages: a very low loss rate compared with those of other existing ordinary absorbents or extracting agents due to the very low vapor pressure; high safety with no danger of explosion; regenerability by a simple stripping process; and easiness of separation from an olefin sample.

Hereinafter, the present invention will be specifically described by reference to examples, which are provided only to describe the present invention in more detail. It will be appreciated by those of ordinary skill in the art that these examples do not limit the scope of the invention in any way.

EXAMPLES

Example 1

Preparation of Pyrrolidinium-based and Piperidinium-based Ionic Liquids 1-alkylpyrrolidine and 1-alkylpiperidine were reacted with dialkylphosphite or trialkylphosphate in order to prepare the pyrrolidinium-based and piperidinium-based ionic liquids used in the present invention.

<1-1> Synthesis of N,N-butylethylpyrrolidinium ethylphosphite

In a 500 ml two-necked flask with a reflux condenser, 60 g of 1-butylpyrrolidine was reacted with 78 g of diethylphosphite under stirring at 80° C. for 12 hrs. After the reaction was terminated, the reactant was washed several times with ethylacetate or diethylether to remove the unreacted 1-butylpyrrolidine and diethylphosphite. The remaining ionic liquid was vacuum dried at 60° C. to obtain the title compound (yield: 98%).

A variety of dialkylpyrrolidinium alkylphosphites were synthesized in a similar manner as described above.

<1-2> Synthesis of N,N-ethylmethylpyrrolidinium diethylphosphate

In a 500 ml two-necked flask with a reflux condenser, 60 g of 1-methylpyrrolidine was reacted with 154 g of triethylphosphate by stirring at 80° C. for 12 hrs. After the reaction was terminated, the reactant was washed several times with ethylacetate or diethylester to remove the unreacted 1-methylpyrrolidine and triethylphosphate. The remaining ionic liquid was vacuum dried at 60° C. to obtain the title compound (yield: 95%).

A variety of dialkylpyrrolidinium dialkylphosphates were synthesized in a similar manner as described above.

<1-3> Synthesis of N,N-ethylmethylpiperidinium ethylphosphite

In a 500 ml two-necked flask with reflux condenser, 60 g of 1-methylpiperidine was reacted with 100 g of diethylphosphite by stirring at 80° C. for 12 hrs. After the reaction was terminated, the reactant was washed several times with ethylacetate or diethylether to remove the unreacted 1-methylpiperidine and diethylphosphite. The remaining ionic liquid was vacuum dried at 60° C. to obtain the title compound (yield: 98%).

A variety of dialkylpiperidinium alkylphosphites were synthesized in a similar manner as described above.

<1-4> Synthesis of N,N-ethylmethylpiperidinium diethylphosphate

In a 500 ml two-necked flask with reflux condenser, 60 g of 1-butylpiperidine was reacted with 93 g of triethylphosphate by stirring at 80° C. for 12 hrs. After the reaction was terminated, the reactant was washed several times with ethylacetate or diethylether to remove the unreacted 1-butylpiperidine and triethylphosphate. The remaining ionic liquid was vacuum dried at 60° C. to obtain the title compound (yield: 93%).

A variety of dialkylpiperidinium dialkylphosphates were synthesized in a similar manner as described above.

Example 2

2.0 g of N,N-ethylmethylpyrrolidinium ethylphosphite, synthesized by reacting N,N-ethylmethylpyrrolidine with diethylphosphite using the same procedure described in Example 1 above, was mixed with 0.4 g of CuCl to prepare a pyrrolidinium-based absorbent. In the prepared pyrrolidinium-based ionic liquid, 1 g of isoprene sample comprising 1,000 ppm of each of $C_5$ acetylene, i.e., isopropenylacetylene (IPA) and 2-butyne (2-BT) and 5,000 ppm of n-heptane as an internal standard material was added at 25° C. and stirred for 1 min. at the same temperature. After stirring, the upper and lower layer liquids were each analyzed by using chromatography (model 6890 N, Agilent) with a HP-PLOT column and 400 MHz $^1$H NMR (Brucker). As a result, of the isoprene sample, 100% of isopropenylacetylene (IPA), 31% of 2-BT, and 0.05% of isoprene were detected in the lower layer liquid. The above results show that a very small amount of acetylene contained in olefin can be effectively extracted by the pyrrolidinium-based ionic liquid according to the present invention.

Example 3

2.0 g of N,N-ethylmethylpiperidinium ethylphosphite synthesized according to Example 1 was mixed with 0.4 g of CuCl to prepare a piperidinium-based ionic liquid. In the prepared piperidinium-based ionic liquid, 1 g of isoprene sample comprising 1,000 ppm of each of $C_5$ acetylene, i.e., isopropenylacetylene (IPA) and 2-butyne (2-BT) and 5,000 ppm of n-heptane as an internal standard material was added at 25° C. and stirred for 1 min. at the same temperature. After stirring, the upper and lower layer liquids were each analyzed by using chromatography (model 6890 N, Agilent) with a HP-PLOT column and 400 MHz $^1$H NMR (Brucker). As a result, of the isoprene sample, 100% of isoprophenylacetylene (IPA), 28% of 2-BT, and 0.07% of isoprene were detected in the lower layer liquid. The above results show that a very small amount of acetylene contained in olefin can be effectively extracted by the piperidinium-based ionic liquid according to the present invention.

Examples 4-9

Extraction experiments were conducted under the same conditions as in Example 2, except that different types of pyrrolidinium-based ionic liquids of Formula 2 were used as shown in Table 1 below. The results from the experiments are summarized in Table 1.

TABLE 1

| Example | Type of ionic liquid | | | Removal rate of acetylene(%) | |
| --- | --- | --- | --- | --- | --- |
| | $R^1$ | $R^2$ | Y | IPA | 2-BT |
| 4 | $CH_3$ | $C_2H_5$ | $P(H)(OC_2H_5)O_2$ | 100 | 31 |
| 5 | $CH_3$ | $C_4H_9$ | $P(H)(OC_4H_9)O_2$ | 100 | 33 |
| 6 | $C_4H_9$ | $CH_3$ | $P(H)(OCH_3)O_2$ | 100 | 33 |
| 7 | $CH_3$ | $CH_3$ | $P(O)(OCH_3)_2O$ | 97 | 27 |
| 8 | $CH_3$ | $C_2H_5$ | $P(O)(OC_2H_5)_2O$ | 98 | 28 |
| 9 | $C_4H_9$ | $CH_3$ | $P(O)(OC_4H_9)_2O$ | 100 | 29 |

Examples 10-15

Extraction experiments were conducted under the same conditions as in Example 3, except that different types of piperidinium-based ionic liquids of Formula 3 were used as shown in Table 2 below. The results from the experiments are summarized in Table 2.

TABLE 2

| Example | Type of ionic liquid | | | Removal rate of acetylene(%) | |
| --- | --- | --- | --- | --- | --- |
| | $R^1$ | $R^2$ | Y | IPA | 2-BT |
| 10 | $CH_3$ | $C_2H_5$ | $P(H)(OC_2H_5)O_2$ | 100 | 27 |
| 11 | $CH_3$ | $C_4H_9$ | $P(H)(OC_4H_9)O_2$ | 100 | 30 |
| 12 | $C_4H_9$ | $CH_3$ | $P(H)(OCH_3)O_2$ | 100 | 31 |
| 13 | $CH_3$ | $CH_3$ | $P(O)(OCH_3)_2O$ | 97 | 27 |
| 14 | $CH_3$ | $C_2H_5$ | $P(O)(OC_2H_5)_2O$ | 98 | 27 |
| 15 | $C_4H_9$ | $CH_3$ | $P(O)(OC_4H_9)_2O$ | 99 | 28 |

Examples 16-21

Extraction experiments were conducted under the same conditions as in Example 2, except that different amounts of CuCl were added in 100 parts by weight of the pyrrolidinium-based ionic liquid as shown in Table 3 below. The results from the experiments are summarized in Table 3.

TABLE 3

| Example | Content of CuCl (part by weight) | Removal rate of acetylene (%) | |
| --- | --- | --- | --- |
| | | IPA | 2-BT |
| 16 | 5 | 81 | 20 |
| 17 | 10 | 95 | 23 |
| 18 | 15 | 100 | 27 |
| 19 | 20 | 100 | 31 |
| 20 | 25 | 100 | 38 |
| 21 | 30 | 100 | 45 |

Examples 22-27

Extraction experiments were conducted under the same conditions as in Example 3, except that different amounts of CuCl were added in 100 parts by weight of the piperidinium-based ionic liquid as shown in Table 4 below. The results from the experiments are summarized in Table 4.

TABLE 4

| Example | Content of CuCl (part by weight) | Removal rate of acetylene (%) IPA | 2-BT |
|---|---|---|---|
| 22 | 5 | 75 | 18 |
| 23 | 10 | 89 | 20 |
| 24 | 15 | 96 | 26 |
| 25 | 20 | 100 | 28 |
| 26 | 25 | 100 | 36 |
| 27 | 30 | 100 | 41 |

Examples 28-29

Extraction experiments were conducted under the same conditions as in Example 2, except that different types of CuX were added in the pyrrolidinium-based ionic liquid as shown in Table 5 below. The results from the experiments are summarized in Table 5.

TABLE 5

| Example | CuX | Removal rate of acetylene (%) IPA | 2-BT |
|---|---|---|---|
| 28 | CuBr | 100 | 36 |
| 29 | CuI | 100 | 40 |

Examples 30-31

Extraction experiments were conducted under the same conditions as in Example 3, except that different types of CuX were added in the piperidinium-based ionic liquid as shown in Table 6 below. The results from the experiments are summarized in Table 6.

TABLE 6

| Example | CuX | Removal rate of acetylene (%) IPA | 2-BT |
|---|---|---|---|
| 30 | CuBr | 100 | 35 |
| 31 | CuI | 100 | 38 |

Examples 32-34

Extraction experiments were conducted under the same conditions as in Example 2, except that mixtures of two different types of pyrrolidinium-based ionic liquids A and B (1.0 g each) were used as shown in Table 7 below. The results from the experiments are summarized in Table 7.

TABLE 7

| | Pyrrolidinium-based ionic liquid | | Removal rate of acetylene (%) | |
|---|---|---|---|---|
| Example | A | B | IPA | 2-BT |
| 32 | N,N-dibutylpyrrolidinium butylphosphite | N,N-butylmethylpyrrolidinium butylphosphite | 98 | 28 |
| 33 | N,N-dimethylpyrrolidinium methylphosphite | N,N-ethylmethylpyrrolidinium ethylphosphite | 97 | 26 |
| 34 | N,N-ethylmethylpyrrolidinium diethylphosphate | N,N-butylmethylpyrrolidinium dibutylphosphate | 97 | 26 |

Examples 35-37

Extraction experiments were conducted under the same conditions as in Example 3, except that mixtures of two different types of piperidinium-based ionic liquids A and B (1.0 g each) were used as shown in Table 8 below. The results from the experiments are summarized in Table 8.

TABLE 8

| | Piperidinium-based ionic liquid | | Removal rate of acetylene (%) | |
|---|---|---|---|---|
| Example | A | B | IPA | 2-BT |
| 35 | N,N-dibutylpiperidiniuim butylphosphite | N,N-butylmethylpiperidinium butylphosphite | 97 | 27 |
| 36 | N,N-dimethylpiperidinium methylphosphite | N,N-ethylmethylpiperidinium ethylphosphite | 95 | 25 |
| 37 | N,N-ethylmethylpiperidinium diethylphosphate | N,N-butylmethylpiperidinium dibutylphosphate | 95 | 24 |

Examples 38-43

Extraction experiments were conducted under the same conditions as in Example 2, except that different amounts of sample were added in the pyrrolidinium-based ionic liquid as shown in Table 9 below. The results from the experiments are summarized in Table 9.

TABLE 9

| Example | Amount of sample (olefin)(g)/ amount of ionic liquid(g) | Removal rate of acetylene (%) IPA | 2-BT |
|---|---|---|---|
| 38 | 0.20 | 100 | 50 |
| 39 | 0.50 | 100 | 31 |
| 40 | 1.00 | 92 | 25 |
| 41 | 1.50 | 86 | 22 |
| 42 | 2.00 | 79 | 19 |
| 43 | 5.00 | 60 | 15 |

Examples 44-49

Extraction experiments were conducted under the same conditions as in Example 3, except that different amounts of the sample were added in the piperidinium-based ionic liquid as shown in Table 10 below. The results from the experiments are summarized in Table 10.

TABLE 10

| Example | Amount of sample (olefin)(g)/ amount of ionic liquid(g) | Removal rate of acetylene(%) IPA | 2-BT |
|---|---|---|---|
| 44 | 0.20 | 100 | 48 |
| 45 | 0.50 | 100 | 28 |
| 46 | 1.00 | 90 | 23 |
| 47 | 1.50 | 82 | 19 |
| 48 | 2.00 | 73 | 16 |
| 49 | 5.00 | 58 | 13 |

Examples 50-55

Extraction experiments were conducted under the same conditions as in Example 2, except that different types of pyrrolidinium-based ionic liquids and samples were used as shown in Table 11 below. The results from the experiments are summarized in Table 11. The amount of CuCl added in 100 parts by weight of the pyrrolidinium-based ionic liquid is 20 parts by weight. The ethylene, propylene and 1-butene samples comprise 1,000 ppm of each of the acetylene, propylene(methylacetylene) and 1-butene(ethylacetylene), respectively.

TABLE 11

| Example | Sample | Ionic liquid | Removal rate of acetylene (%) |
|---|---|---|---|
| 50 | ethylene | N,N-butylethylpyrrolidinium ethylphosphite | 100 |
| 51 | propylene | N,N-dibutylpyrrolidinium butylphosphite | 100 |
| 52 | 1-butene | N,N-ethylmethylpyrrolidinium ethylphosphite | 100 |
| 53 | ethylene | N,N-dibutylpyrrolidinium dibutylphosphate | 98 |
| 54 | propylene | N,N-ethylmethylpyrrolidinium diethylphosphate | 97 |
| 55 | 1-butene | N,N-dimethylpyrrolidinium dimethylphosphate | 96 |

Examples 56-61

Extraction experiments were conducted under the same conditions as in Example 3, except that different types of piperidinium-based ionic liquids and samples were used as shown in Table 12 below. The results from the experiments are summarized in Table 12. The amount of CuCl added in 100 parts by weight of the piperidinium-based ionic liquid is 20 parts by weight. The ethylene, propylene and 1-butene samples comprise 1,000 ppm of each of the acetylene, propylene(methylacetylene) and 1-butene(ethylacetylene), respectively.

TABLE 12

| Example | Sample | Ionic liquid | Removal rate of acetylene (%) |
|---|---|---|---|
| 56 | ethylene | N,N-butylethylpiperidinium ethylphosphite | 100 |
| 57 | propylene | N,N-dibutylpiperidinium butylphosphite | 100 |
| 58 | 1-butene | N,N-ethylmethylpiperidinium ethylphosphite | 100 |
| 59 | ethylene | N,N-dibutylpiperidinium dibutylphosphate | 97 |
| 60 | propylene | N,N-ethylmethylpiperidinium diethylphosphate | 95 |
| 61 | 1-butene | N,N-dimethylpiperidinium dimethylphosphate | 94 |

Examples 62-65

Extraction experiments were conducted under the same conditions as in Example 2, except that different extraction temperatures were used as shown in Table 13 below. The results from the experiments are summarized in Table 13.

TABLE 13

| Example | Extraction temperature (° C.) | Removal rate of acetylene (%) IPA | 2-BT |
|---|---|---|---|
| 62 | 20 | 100 | 35 |
| 63 | 30 | 98 | 28 |
| 64 | 40 | 96 | 24 |
| 65 | 50 | 90 | 19 |

Examples 66-70

Extraction experiments were conducted under the same conditions as in Example 3, except that different extraction temperatures were used as shown in Table 14 below. The results from the experiments are summarized in Table 14.

TABLE 14

| Example | Extraction temperature (° C.) | Removal rate of acetylene (%) IPA | Removal rate of acetylene (%) 2-BT |
| --- | --- | --- | --- |
| 67 | 20 | 100 | 33 |
| 68 | 30 | 96 | 24 |
| 69 | 40 | 92 | 22 |
| 70 | 50 | 89 | 17 |

Examples 71-75

After conducting extraction experiments under the same conditions as in Example 2, hydrocarbons (olefin and acetylene) extracted from the pyrrolidinium-based ionic liquid were stripped under reduced pressure. The results are summarized in Table 15 below. Stripping was carried out at the temperatures and pressures described in Table 15 below.

TABLE 15

| Example | Stripping temperature (° C.) | Stripping pressure (mmHg) | Stripping rate (%) IPA | Stripping rate (%) 2-BT |
| --- | --- | --- | --- | --- |
| 71 | 20 | 50 | 85 | 90 |
| 72 | 50 | 20 | 100 | 100 |
| 73 | 50 | 70 | 96 | 98 |
| 74 | 70 | 50 | 100 | 100 |
| 75 | 100 | 100 | 100 | 100 |

Examples 76-80

After conducting extraction experiments under the same conditions as in Example 2, hydrocarbons (olefin and acetylene) extracted from the piperidinium-based ionic liquid were stripped under reduced pressure. The results are summarized in Table 16 below. Stripping was carried out at the temperatures and pressures described in Table 16 below.

TABLE 16

| Example | Stripping temperature (° C.) | Stripping pressure (mmHg) | Stripping rate (%) IPA | Stripping rate (%) 2-BT |
| --- | --- | --- | --- | --- |
| 76 | 20 | 50 | 82 | 88 |
| 77 | 50 | 20 | 100 | 100 |
| 78 | 50 | 70 | 94 | 96 |
| 79 | 70 | 50 | 100 | 100 |
| 80 | 100 | 100 | 100 | 100 |

Although specific embodiments of the present invention have been described in detail as above, it will be appreciated by those of ordinary skill in the art that such detailed descriptions are merely possible embodiments and do not limit the scope of the invention. The substantial scope of the present invention will be defined by the claims and the equivalents thereof.

What is claimed:

1. A method of purifying olefin, comprising the steps of:
   1) preparing an ionic liquid mixture comprising copper (I) halide by dissolving copper (I) halide represented by Formula 1 in a pyrrolidinium-based ionic liquid represented by Formula 2 or a piperidinium-based ionic liquid represented by Formula 3; and
   2) contacting said ionic liquid mixture comprising copper (I) halide with olefin to remove acetylenic compounds from the olefin

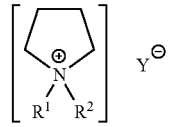
<Formula 1>
<Formula 2>

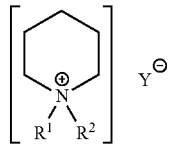
<Formula 3> wherein X is Cl, Br or I,
  $R^1$ is a $C_1 \sim C_6$ alkyl group,
  $R^2$ is a $C_1 \sim C_6$ alkyl group or alkoxy group,
  Y is a phosphite anion represented by Formula 4 or a phosphate anion represented by Formula 5,

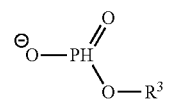
<Formula 4>

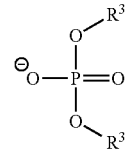
<Formula 5> wherein $R^3$ is a $C_1 \sim C_6$ alkyl group.

2. The method of claim 1, wherein in step 1), the copper (I) halide of Formula 1 is dissolved in an amount of from 5 to 50 parts by weight per 100 parts by weight of the pyrrolidinium-based ionic liquid of Formula 2 or the piperidinium-based ionic liquid of Formula 3.

3. The method of claim 1, wherein in step 1), the pyrrolidinium-based ionic liquid or piperidinium-based ionic liquid is used alone or in the form of a mixture of two or more.

4. The method of claim 1, wherein the ionic liquid mixture comprising copper (I) halide prepared in step 1) is represented by Formula 6 or Formula 7

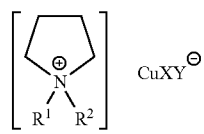
<Formula 6>

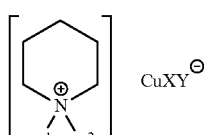
<Formula 7> wherein X, $R^1$, $R^2$ and Y are as defined in claim 1.

5. The method of claim 1, wherein in step 2), the olefin is mixed in an amount of from 20 to 500 parts by weight per 100 parts by weight of the ionic liquid mixture comprising copper (I) halide.

6. The method of claim 1, wherein in step 2), the ionic liquid mixture comprising copper (I) halide is reacted with olefin by stirring at 0-100° C. for 0.5-1 hr.

7. The method of claim 1, wherein in step 2), where the olefin is a $C_2$~$C_4$ olefin in a gaseous state and said reaction is carried out by an absorption process after mixing the ionic liquid mixture comprising copper (I) halide with the olefin.

8. The method of claim 1, wherein in step 2), where the olefin is a $C_5$ olefin in a liquid state and said reaction is carried out either by an extraction process after mixing the ionic liquid mixture comprising copper (I) halide with the olefin or by an absorption process after evaporating the olefin.

9. The method of claim 1, wherein in step 2), the acetylenic compound is selected from the group consisting of acetylene, methyl acetylene, 1-butyne, isopropenylacetylene and a mixture thereof.

10. The method of claim 1 further comprising:
following step 2), retrieving the ionic liquid mixture comprising copper (I) halide and regenerating the mixture by stripping under conditions of 20 to 120° C. and 1 to 200 mmHg.

11. A pyrrolidinium-based ionic liquid mixture comprising copper (I) halide represented by Formula 6, as an absorbent or an extracting agent for removing an acetylenic compound from olefin:

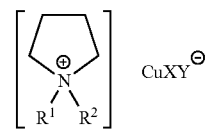

<Formula 6> wherein X, $R^1$, $R^2$ and Y are as defined in claim 1.

12. A piperidinium-based ionic liquid mixture comprising copper (I) halide represented by Formula 7, as an absorbent or an extracting agent for removing an acetylenic compound from olefin:

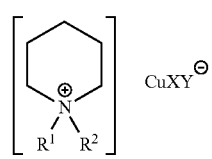

<Formula 7> wherein X, $R^1$, $R^2$ and Y are as defined in claim 1.

* * * * *